(12) United States Patent
Nishihara et al.

(10) Patent No.: US 9,757,091 B2
(45) Date of Patent: Sep. 12, 2017

(54) ULTRASOUND DIAGNOSIS APPARATUS, MEDICAL IMAGE-PROCESSING APPARATUS, AND METHOD OF PROCESSING MEDICAL IMAGES

(71) Applicant: Toshiba Medical Systems Corporation, Otawara-shi (JP)

(72) Inventors: Kuramitsu Nishihara, Otawara (JP); Tomohisa Imamura, Nasushiobara (JP); Takuya Sasaki, Nasu-machi (JP); Yuko Takada, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 83 days.

(21) Appl. No.: 14/315,983

(22) Filed: Jun. 26, 2014

(65) Prior Publication Data

US 2015/0018681 A1 Jan. 15, 2015

(30) Foreign Application Priority Data

Jul. 12, 2013 (JP) .................................. 2013-147048

(51) Int. Cl.
*A61B 8/08* (2006.01)

(52) U.S. Cl.
CPC ............ *A61B 8/5207* (2013.01); *A61B 8/085* (2013.01); *A61B 8/5223* (2013.01)

(58) Field of Classification Search
CPC ...... A61B 8/085; A61B 8/5207; A61B 8/5223
See application file for complete search history.

(56) References Cited

U.S. PATENT DOCUMENTS

| | | | | |
|---|---|---|---|---|
| 2004/0081340 A1* | 4/2004 | Hashimoto | ............. | A61B 8/00 382/128 |
| 2006/0165307 A1* | 7/2006 | Kondo | ................. | G06T 3/4084 382/249 |
| 2006/0274924 A1* | 12/2006 | West | ..................... | A61N 5/103 382/131 |

(Continued)

FOREIGN PATENT DOCUMENTS

JP 2012-101073 5/2012

*Primary Examiner* — Baisakhi Roy
(74) *Attorney, Agent, or Firm* — Oblon, McClelland, Maier & Neustadt, L.L.P.

(57) ABSTRACT

Ultrasound diagnosis apparatus comprises an image generator, a first structural information acquirer, a second structural information acquirer, and a synthesizer. The image generator generates, based on ultrasound waves transmitted and received in accordance with a plurality of transmission and reception conditions, sets of image data whose images represent at least partially a common area for each of the transmission and reception conditions. The first structural information acquirer acquires tissue-structure information indicative of tissue structures depicted, respectively, in the sets of image data. The second structural information acquirer acquires common structural information indicative of a tissue structure common in the sets of image data, based on the tissue-structure information. The synthesizer changes the method of image-synthesis applied on the sets of image data, a different method for each of the image areas distinguished based on the common structural information, and generates composition image data based on the sets of image data.

15 Claims, 11 Drawing Sheets

(56) References Cited

U.S. PATENT DOCUMENTS

2008/0267482 A1* 10/2008 Abe .................. A61B 8/08
                                                382/131
2012/0114209 A1    5/2012 Kim et al.
2013/0308849 A1* 11/2013 Fei .................. G06T 7/0081
                                                382/131

* cited by examiner

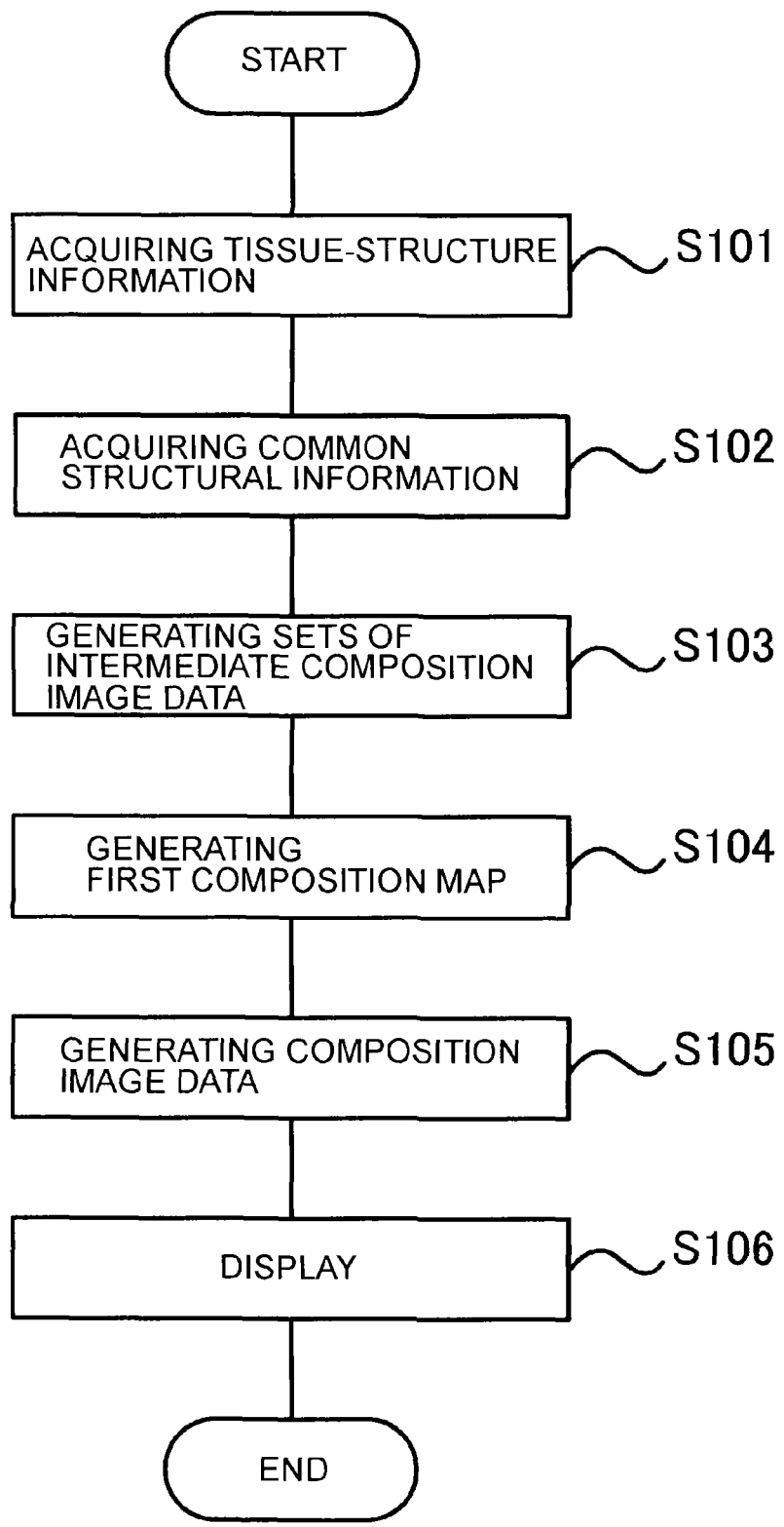

ULTRASOUND DIAGNOSIS APPARATUS, MEDICAL IMAGE-PROCESSING APPARATUS, AND METHOD OF PROCESSING MEDICAL IMAGES

CROSS-REFERENCE TO RELATED APPLICATION

This application is based upon and claims the benefit of priority from Japanese Patent Application No. 2013-147048, filed Jul. 12, 2013; the entire contents all of which are incorporated herein by reference.

FIELD

Embodiments relate to ultrasound diagnosis apparatus, medical image-processing apparatus, and methods of processing medical images.

BACKGROUND

Ultrasound diagnosis apparatus acquires biological information of a subject by sending ultrasound waves into the subject and receiving reflected waves through an ultrasound probe. The ultrasound diagnosis apparatus then generates ultrasound image data, which represent, for example, tissue structures of the subject, based on the acquired biological information.

As for prior-art ultrasound diagnosis apparatuses, there is a technique known as "transmission-reception compound technique". The transmission-reception compound technique is a technique in which ultrasound waves through the subject are transmitted and received based on a plurality of transmission and reception conditions, and a plurality of sets of image data obtained accordingly are then combined to generate composition image data. For example, an ultrasound diagnosis apparatus transmits and receives ultrasound waves through the subject in a plurality of transmission and reception directions as transmission and reception conditions and then combines a plurality of sets of image data thus obtained. In addition, the ultrasound diagnosis apparatus may transmit and receive ultrasound waves of a plurality of transmission and reception frequencies through the subject as transmission and reception conditions and then combine a plurality of sets of image data thus obtained. Furthermore, the ultrasound diagnosis apparatus may generate a set of image data for each of a plurality of received-signal processing conditions as transmission and reception conditions and may combine a plurality of sets of image data thus obtained.

In such a transmission-reception compound technique, for example, the ultrasound diagnosis apparatus calculates arithmetic means for the pixel values of a plurality of sets of image data to determine pixel values for composition image data so as to generate the composition image data with reduced speckle noise.

Moreover, by the transmission-reception compound technique, the ultrasound diagnosis apparatus may emphasize a particular tissue structure depicted in an image. In such a case, the ultrasound diagnosis apparatus selects maximum values from the pixel values of a plurality of sets of image data and sets the maximum values as pixel values for composition image data so as to generate the composition image data with an enhanced contour for the tissue structure depicted in an image. In the specification, this method of image-synthesis is referred to as "highest selection".

However, the image generated through the arithmetic means as composition image data has been such that the difference in pixel values representing the contour and the other part is smaller than that of the image generated through the highest selection as composition image data. As a result, the image generated through the arithmetic means as composition image data is rather difficult for the user to visually recognize the contour. On the other hand, the composition image data generated through the highest selection include more speckle noise than the composition image data generated through the arithmetic means. This means that images from the composition image data generated through the highest selection show unevenness in pixel values for the same tissue. Accordingly, the images are difficult for the user to visually recognize the same tissue.

BRIEF DESCRIPTION OF THE DRAWINGS

FIG. 9 is a flowchart showing actions taken by the medical image-processing apparatus as an embodiment.

DETAILED DESCRIPTION

An ultrasound diagnosis apparatus as an embodiment comprises an image generator, a first structural information acquirer, a second structural information acquirer, and a synthesizer. The image generator generates, based on ultrasound waves transmitted and received in accordance with a plurality of transmission and reception conditions, sets of image data whose images represent at least partially a common area for each of the transmission and reception conditions. The first structural information acquirer acquires tissue-structure information indicative of tissue structures depicted, respectively, in the sets of image data. The second structural information acquirer acquires common structural information indicative of a tissue structure common in the sets of image data, based on the tissue-structure information. The synthesizer changes the method of image-synthesis applied on the sets of image data, a different method for each of the image areas distinguished based on the common structural information, and generates composition image data based on the sets of image data.

First Embodiment

[Configuration]

Figure 1:
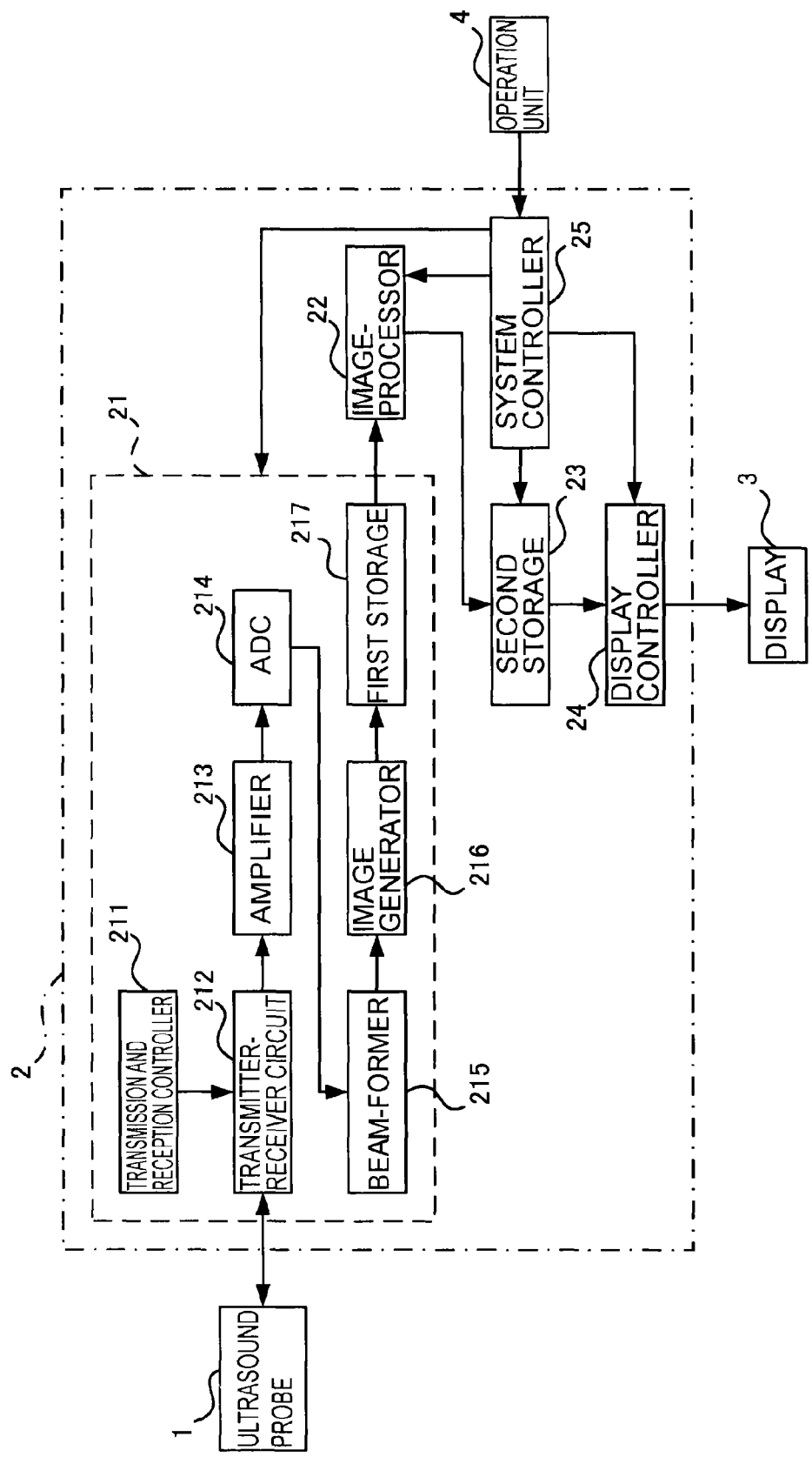
FIG. 1 is a block diagram representing the configuration of an ultrasound diagnosis apparatus as an embodiment.

FIG. 1 is a block diagram representing the configuration of an ultrasound diagnosis apparatus as this embodiment. The ultrasound diagnosis apparatus comprises an ultrasound probe 1, a main body 2, a display 3, and an operation unit 4.

(Ultrasound Probe 1)

The ultrasound probe 1 sends ultrasound waves into the subject, based on pulse signals received from a transmitter-receiver circuit 212, and ultrasound waves are reflected at boundaries of difference in acoustic impedance in the is subject. The ultrasound probe 1 receives reflected waves from the subject. The ultrasound probe 1 has a plurality of ultrasound transducers. The ultrasound probe 1 used may be a 1D array probe, whose plurality of ultrasound transducers are disposed in a line in scanning direction, or a 2D array probe, whose plurality of ultrasound transducers are disposed two-dimensionally. The ultrasound probe 1 converts pulse signals received from the transmitter-receiver circuit 212 into acoustic signals by the ultrasound transducers and sends them into the subject. In addition, the ultrasound probe 1 receives reflected waves from the subject with the ultrasound transducers, converts them into electrical signals (echo signals), and outputs them to the transmitter-receiver circuit 212.

(Main Body 2)

The main body 2 comprises a scanner 21, an image-processor 22, a second storage 23, a display controller 24, and a system controller 25.

(Scanner 21)

The scanner 21 transmits and receives ultrasound waves through the subject based on a plurality of transmission and reception conditions and generates image data that represent tissue structures of the subject for each of the transmission and reception conditions. In addition, the scanner 21 generates image data based on a plurality of transmission and reception directions, a plurality of transmission and reception frequencies, or a plurality of reception-signal processing conditions as the transmission and reception conditions. The scanner 21 comprises a transmission and reception controller 211, a transmitter-receiver circuit 212, an amplifier 213, an ADC (Analog-to-Digital Converter) 214, a beam-former 215, an image generator 216, and a first storage 217.

(Transmission and Reception Controller 211)

The transmission and reception controller 211 outputs control signals that indicate conditions for the transmission and reception of ultrasound waves, to the transmitter-receiver circuit 212. The transmission and reception conditions include a plurality of transmission and reception directions or a plurality of transmission and reception frequencies. For example, the transmission and reception controller 211 receives transmission and reception conditions set by the user, from the system controller 25. The control signals output from the transmission and reception controller 211 include transmission and reception direction information that is used for modifying the strength and the application timing of pulse signals that are output from the transmitter-receiver circuit 212 to the ultrasound probe 1, each signal for a corresponding one of the ultrasound transducers. As a result, the ultrasonic beam being emitted from the ultrasound probe 1 is controlled with respect to its direction and angle. The transmission and reception controller 211 stores, in advance, predetermined sets of transmission and reception direction information.

In addition, the control signals output from the transmission and reception controller 211 may include various sets of transmission and reception frequency information that indicate frequencies for pulse signals that are output from the transmitter-receiver circuit 212 to the ultrasound probe 1. As a result, the ultrasound waves being emitted from the ultrasound probe 1 are controlled with respect to their frequency. The transmission and reception controller 211 stores, in advance, predetermined sets of transmission and reception frequency information.

(Transmitter-Receiver Circuit 212)

The transmitter-receiver circuit 212 outputs pulse signals to the ultrasound probe 1, based on control signals received from the transmission and reception controller 211. For example, the transmitter-receiver circuit 212 outputs a pulse signal for each individual path (channel) that leads to a corresponding one of the ultrasound transducers in order to emit ultrasound waves that are beam-formed at a predetermined focal point (i.e., transmission-beam-formed). In addition, the transmitter-receiver circuit 212 receives echo signals from each of the ultrasound transducers of the ultrasound probe 1 and outputs them to the amplifier 213.

(Amplifier 213)

The amplifier 213 amplifies the echo signals received from the ultrasound probe 1 and outputs them to the ADC 214. The amplifier 213 is configured to include, for example, a preamplifier circuit.

(ADC 214)

The ADC 214 converts the echo signals, which have been amplified by the amplifier 213, into digital signals and outputs them to the beam-former 215.

(Beam-Former 215)

The beam-former 215 executes delay-processing and addition-processing on the digital signals received from the ADC 214 in order to calculate phased signals (i.e., reception-beam-formed). The beam-former 215 outputs the phased signals to the image generator 216 as reception signals.

(Image generator 216)

The image generator 216 generates, based on ultrasound waves transmitted and received in accordance with a plurality of transmission and reception conditions, sets of image data whose images represent at least partially a common area for each of the transmission and reception conditions. The image generator 216, as it receives reception signals from the beam-former 215, creates an image from the amplitude information of the received signals. At this instant, the image generator 216 processes the reception signals with a band-pass filter and detects the envelope of the signals, which have been band-pass filtered. The image generator 216 then executes compression-processing by logarithmic transformation on the data detected from the waves. In addition, the image generator 216 may execute a process of spatial filtering on the reception signals, the process being smoothing or sharping with respect to a predetermined direction. The image generator 216 outputs the processed data as image data to the first storage 217. Incidentally, the image generator 216 may generate a set of image data for each of a plurality of reception-signal processing conditions as the transmission and reception conditions. The image generator 216 stores, in advance, various sets of reception-signal processing conditions, which include, for example, processing conditions for the process of spatial filtering.

(First Storage 217)

The first storage 217 receives image data from the image generator 216 and stores them.

Incidentally, all parts of the scanner 21 mentioned above function in accordance with each of the transmission and reception conditions. As a result, the image generator 216 generates a set of image data for each of the transmission and reception conditions, i.e., a plurality of transmission and reception directions, a plurality of transmission and reception frequencies or a plurality of reception-signal processing conditions provided as the transmission and reception conditions. The first storage 217, therefore, stores a set of image data for each of the transmission and reception conditions.

(Image-Processor 22)

Figure 2:
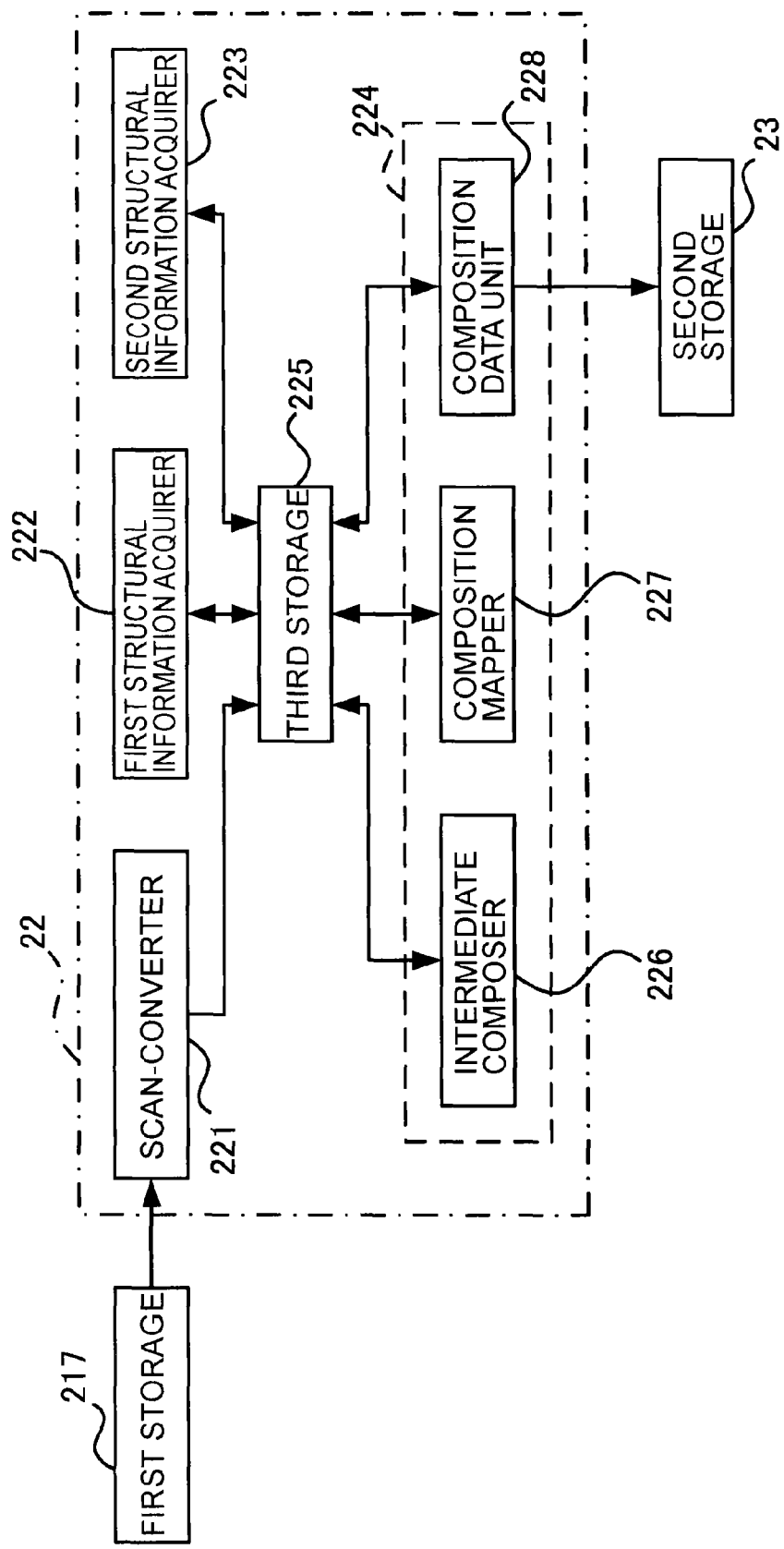
FIG. 2 is a block diagram representing the configuration of an ultrasound diagnosis apparatus as an embodiment.

The image-processor 22 comprises a scan-converter 221, a first structural information acquirer 222, a second structural information acquirer 223, a synthesizer 224, and a third storage 225. FIG. 2 is a block diagram representing the configuration of the image-processor 22.

(Scan-Converter 221)

The scan-converter 221 reads image data out of the first storage 217. The scan-converter 221 converts the image data that correspond to a column of signals for a scanning line into data to be displayed in a coordinate system. The scan-converter 221 outputs the converted image data to the third storage 225, which stores them.

(First Structural Information Acquirer 222)

The first structural information acquirer 222 acquires tissue-structure information indicative of tissue structures depicted, respectively, in a plurality of sets of image data. For example, the first structural information acquirer 222 reads image data out of the third storage 225 and acquires tissue-structure information indicative of tissue structures depicted in the image data. The first structural information acquirer 222 also acquires first structural information for each set of image data (image data per frame). For example, the first structural information acquirer 222 executes on the image data edge-detection processing based on such edge-detection algorithms as Sobel, Laplacian, and Canny. As a result, tissue-structure information is acquired as contour information which provides enhanced pixel values for pixels representing the part along the contour of a tissue structure. In addition, the first structural information acquirer 222 may acquire structure tensor for the image data and may output the acquired structure tensor as tissue-structure information to the third storage 225. In the structure tensor, the contour in the image data is indicated by the magnitudes of specific values. Furthermore, the first structural information acquirer 222 may execute, on the image data, Wavelet conversion and such multi-resolution analysis as Laplacian Pyramid and may then acquire tissue-structure information for a predetermined layer by using the above-mentioned methods. Incidentally, the first structural information acquirer 222, after acquiring the contour, may execute a process of spatial filtering for emphasizing the contour. In addition, the first structural information acquirer 222 may execute normalization-processing on the tissue-structure information. Furthermore, the first structural information acquirer 222 may execute threshold-processing on the tissue-structure information for converting the tissue-structure information into binary information. In this case, for example, the pixel value for pixels representing the contour may be set at "1" while the pixel value for pixels representing other than the contour may be set at "0". The first structural information acquirer 222 outputs the acquired tissue-structure information to the third storage 225, which stores it.

(Second Structural Information Acquirer 223)

The second structural information acquirer 223 acquires common structural information indicative of a tissue structure common in the sets of image data, based on the tissue-structure information. In this case, the second structural information acquirer 223 reads more than one set of tissue-structure information out of the third storage 225. With respect to the sets of tissue-structure information read out, the second structural information acquirer 223 multiplies the pixel values of pixels that are at the same coordinates in the sets of image data. The second structural information acquirer 223 executes this multiplication for each pixel and acquires common structural information, and for example, the pixel values of pixels representing the contour in the image data are emphasized in the contour information. The second structural information acquirer 223 emphasizes the pixel values of pixels representing the common contour, which is a contour common in the sets of image data, by multiplying the pixel values in the contour information. As a result, in the common contour information as common structural information, the pixel values of pixels for the common contour are enhanced much more than the pixel values of pixels for other than the common contour. The positions of the pixels whose values have been emphasized represent the position of the common contour. Additionally, the second structural information acquirer 223 may execute normalization-processing on the acquired common structural information. The second structural information acquirer 223 outputs the acquired common structural information to the third storage 225, which stores it.

In addition, if the first structural information is binary information, the second structural information acquirer 223 executes AND operation on the pixel values of pixels that are at the same coordinates in the sets of tissue-structure information read out. The second structural information acquirer 223 executes this AND operation for each pixel and acquires common structural information. If the tissue-structure information is binary information, it has "1" as the pixel value for the pixels representing a tissue structure in the image data and "0" as the pixel value for the pixels representing no tissue structure. The second structural information acquirer 223 executes AND operation on the pixel values at the same coordinates in the sets of tissue-structure information so as to set the pixel value for pixels representing the common contour, which is a tissue structure common in the sets of image data, at "1" and the pixel value for pixels representing other than the common contour at "0". As a result, the pixel value for pixels representing the common contour is set at "1" in the common structural information. The positions of these pixels represent the position of the common contour. The second structural information acquirer 223 outputs the acquired common structural information to the third storage 225, which stores it.

(Synthesizer 224)

The synthesizer 224 applies different methods of image-synthesis on a plurality of sets of image data, each method to a corresponding one of the image areas distinguished based on the common structural information, in order to generate composition image data based on the sets of image data. For example, to the pixels representing a common structure and to the other of the pixels in a plurality of sets of image data, the synthesizer 224 applies different methods of image-synthesis, respectively, based on the common structural information, in order to combine the sets of image data and generate composition image data. The methods of image-synthesis here include two or more of the following: arithmetic mean in which the means of pixel values in the sets of image data are set as pixel values for the composition image data; highest selection in which the maximum values of pixel values in the sets of image data are set as pixel values for the composition image data; weighting addition in which the values obtained by weighting and adding pixel values in the sets of image data are set as pixel values for the composition image data; median selection in which the median values of pixel values in the sets of image data are set as pixel values for the composition image data; and lowest selection in which the minimum values of pixel values in the sets of image data are set as pixel values for the composition image data. In addition, the synthesizer 224 generates sets of intermediate composition image data, each set being a composition of the sets of image data by a corresponding one of the methods of image-synthesis applied, and generates a first composition map, which relates any one of the sets of intermediate composition image data to the common structural information, and then generates the composition image data based on the first composition map. The synthesizer 224 comprises an intermediate composer 226, a composition mapper 227, and a composition data unit 228.

(Intermediate Composer 226)

The intermediate composer 226 reads sets of image data out of the third storage 225 and generates sets of intermediate composition image data, each set being a composition of the sets of image data by a corresponding one of the methods of image-synthesis applied. The methods of image-synthesis include two or more of the arithmetic mean, highest selection, weighting addition, median selection and lowest selection. In the following descriptive example, the intermediate composition image data are generated based on image data generated in accordance with n types of transmission and reception conditions (n: any natural number that is 2 or larger). For example, the intermediate composer 226 reads n sets of image data out of the third storage 225. The intermediate composer 226, for generating intermediate composition image data by the arithmetic mean of the methods of image-synthesis, executes a masking process that multiplies the pixel values of all pixels in the image data by 1/n. The intermediate composer 226 then adds together the n sets of image data that have been masking-processed so as to generate the intermediate composition image data by the arithmetic mean. In addition, the intermediate composer 226, for generating intermediate composition image data by the highest selection of the methods of image-synthesis, selects the image data whose pixel values are the maximum for the pixels at the same respective coordinates in n sets of image data. The intermediate composer 226 then substitutes the pixel values respectively selected of the pixels in the image data, so as to generate the intermediate composition image data by the highest selection. Furthermore, the intermediate composer 226, for generating intermediate composition image data by the weighting addition, stores in advance a weighting coefficient for each of the n sets of image data and multiplies the pixel values of the pixels in each set of image data by a corresponding weighting factor. The intermediate composer 226 then adds together the n sets of image data after the multiplication, so as to generate the intermediate composition image data by the weighting addition. Moreover, the intermediate composer 226, for generating intermediate composition image data by the median selection of the methods of image-synthesis, selects the image data whose pixel values are the medians for the pixels at the same respective coordinates in the n sets of image data. The intermediate composer 226 then substitutes the pixel values respectively selected of the pixels in the image data, so as to generate the intermediate composition image data by the median selection. Also, the intermediate composer 226, for generating intermediate composition image data by the lowest selection of the methods of image-synthesis, selects the image data whose pixel values are the minimum for the pixels at the same respective coordinates in the n sets of image data. The intermediate composer 226 then substitutes the pixel values respectively selected of the pixels in the image data, so as to generate the intermediate composition image data by the lowest selection. The intermediate composer 226 outputs the generated intermediate composition image data to the third storage 225, which stores them.

For the intermediate composer 226, the methods of image-synthesis are preset to be used for generating intermediate composition image data. For example, the methods of image-synthesis are set for a particular part of the subject to be depicted in image data. Also, the intermediate composer 226 may accept the specifications of the methods of image-synthesis by the user.

(Composition Mapper 227)

The composition mapper 227 generates a first composition map, which indicates intermediate composition image data in relation to respective coordinates. In the composition mapper 227, methods of image-synthesis are preset, for example, one method for the pixels representing a common structure and another for the pixels representing no common structure. These methods of image-synthesis are the methods applied for image-synthesis by the intermediate composer. Furthermore, different methods of image-synthesis are set, respectively, one for the pixels representing a common structure and another for the pixels representing no common structure. The composition mapper 227 reads common structural information and intermediate composition image data out of the third storage 225. The composition mapper 227 relates the coordinates of the pixels representing a common structure, which are indicated in the common structural information, to the pixels at the respective coordinates of the intermediate composition image data by the method of image-synthesis that corresponds to the pixels representing a common structure. In addition, the composition mapper 227 relates the coordinates of the pixels representing no common structure, which are indicated in the common structural information, to the pixels at the respective coordinates of the intermediate composition image data by the method of image-synthesis that corresponds to the pixels representing no common structure. As a result, on the first composition map, sets of intermediate composition image data, each set having been generated by a method of image-synthesis different from the other, are related respectively to the coordinates of the pixels representing a common structure and to the coordinates of the pixels representing no common structure. The composition mapper 227 outputs the generated first composition map to the third storage 225, which stores it.

(Composition Data Unit 228)

The composition data unit 228 generates composition image data based on the first composition map. The composition data unit 228 reads the first composition map and intermediate composition image data out of the third storage 225. The composition data unit 228 executes a process that sets the pixel values of the pixels at the coordinates in the intermediate composition image data that are related to coordinates on the first composition map, as the pixel values of the pixels at the corresponding coordinates in the composition image data. The composition data unit 228 generates composition image data by executing this process for all the coordinates.

Here, on the first composition map, related respectively to the coordinates of the pixels representing a common structure and to the coordinates of the pixels representing no common structure are sets of intermediate composition image data, each set having been generated by a method of image-synthesis different from the other. For the sets of composition image data, therefore, the method of image-synthesis applied to the pixel values in the intermediate composition image data substituting for the pixels representing a common structure is different from the method of image-synthesis applied to the pixel values in the intermediate composition image data substituting for the pixels representing no common structure. For example, on the first composition map, if the intermediate composition image data by the highest selection are related to the coordinates of the pixels representing a common structure, and the intermediate composition image data by the arithmetic mean are related to the coordinates of the pixels representing no common structure, then, for the composition image data, the composition data unit 228 substitutes the pixel values in the intermediate composition image data by the highest selection for the pixels representing a common structure and the pixel values in the intermediate composition image data by the arithmetic mean for the pixels representing no common structure. As a result, the composition image data are generated with the pixel values calculated by the highest selection of the methods of image-synthesis, which is assigned to the pixels representing a common structure, and with the pixel values calculated by the arithmetic mean of the methods, which is assigned to the pixels representing no common structure. This is equivalent to that the composition image data are generated as image data combined by different methods of image-synthesis, one method for the pixels representing a common structure and another for the pixels representing no common structure. The composition data unit 228 outputs the generated composition image data to the second storage 23.

Figure 3:
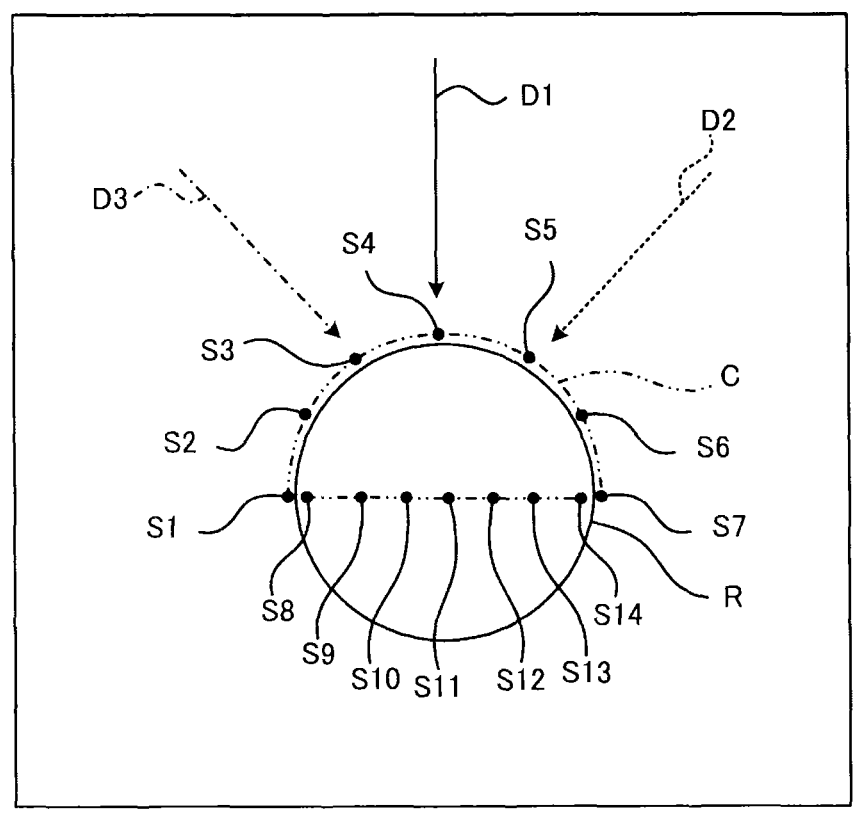
FIG. 3 is a schematic view showing an outline of the ultrasound diagnosis apparatus as an embodiment.
Figure 4:
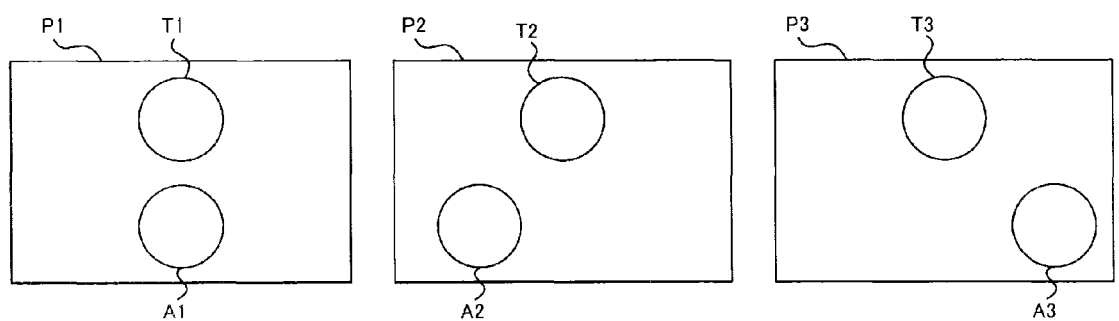
FIG. 4 is a schematic view showing an outline of the ultrasound diagnosis apparatus as an embodiment.

Now, explanation is given of the significance of applying different methods of image-synthesis, respectively, for the pixels representing a common structure and for the pixels representing no common structure. Here, as a descriptive example, image data are generated, based on three transmission and reception directions as transmission and reception conditions. The first structural information acquirer calculates, as tissue-structure information, contour information on the image data, and the second structural information acquirer receives the contour information and acquires, as common structural information, common contour information that is common in the sets of image data. FIG. 3 is a schematic view showing transmission and reception directions of ultrasound waves with respect to a part R having a circular cross-section. FIG. 4 are schematic views, each showing positions where a real image and an artifact are depicted in image data, respectively, in the transmission and reception directions. Image P1 is an image by the image data generated based on transmission and reception direction D1. Real image T1 is a real image depicted in image P1. Artifact A1 is an artifact depicted in image P1. In addition, image P2 is an image by the image data generated based on transmission and reception direction D2. Real image T2 is a real image depicted in image P2. Artifact A2 is an artifact depicted in image P2. In addition, image P3 is an image by the image data generated based on transmission and reception direction D3. Real image T3 is a real image depicted in image P3. Artifact A3 is an artifact depicted in image P3. In image P1, image P2 and image P3, real image T1, real image T2 and real image T3 are depicted at the same coordinates. In addition, since transmission and reception direction D1, transmission and reception direction D2 and transmission and reception direction D3 are different directions from one another, artifact A1, artifact A2 and artifact A3 may be depicted at different positions.

The first structural information acquirer 222 acquires the contour of a tissue structure in each set of image data, and therefore, generates contour information that indicates as contours both the real image and the artifact depicted in the image data. In other words, the contour information includes information that indicates the contours whose coordinate information is both for the real image and the artifacts. The second structural information acquirer 223 acquires common contour information that indicates a common contour, which is the contour common in the sets of image data. In the case of the example shown in FIG. 4, real image T1, real image T2, and real image T3, which are depicted at the same coordinates, are the common contour. The coordinates of real image T1, real image T2, and real image T3 are, therefore, included in the common contour while the coordinates of artifact A1, artifact A2, and artifact A3 are not included in the common contour. As a result, the second structural information can indicate the coordinates of the real image depicted of the part R.

For example, the synthesizer 224 executes image-synthesis by the highest selection on the pixels representing the common contour (real image T1, real image T2, and real image T3) and executes image-synthesis by the arithmetic mean on the pixels representing no common contour. In this process, maximum values existing in real image T1, real image T2 and real image T3 are assigned as the pixel values for the pixels representing the common contour. As a result, large pixel values are assigned to the pixels representing the common contour. As large pixel values are employed in this way, the real image, which is the common contour, is emphasized. On the other hand, for the pixel values of the pixels representing no common contour, employed are the addition mean values of the corresponding pixel values in image P1, image P2 and image P3. As a result, pixel values are reduced for artifact A1, artifact A2 and artifact A3, so the artifacts depicted at coordinates, which are not for the common contour, are reduced in the composition image data.

Figure 5A:
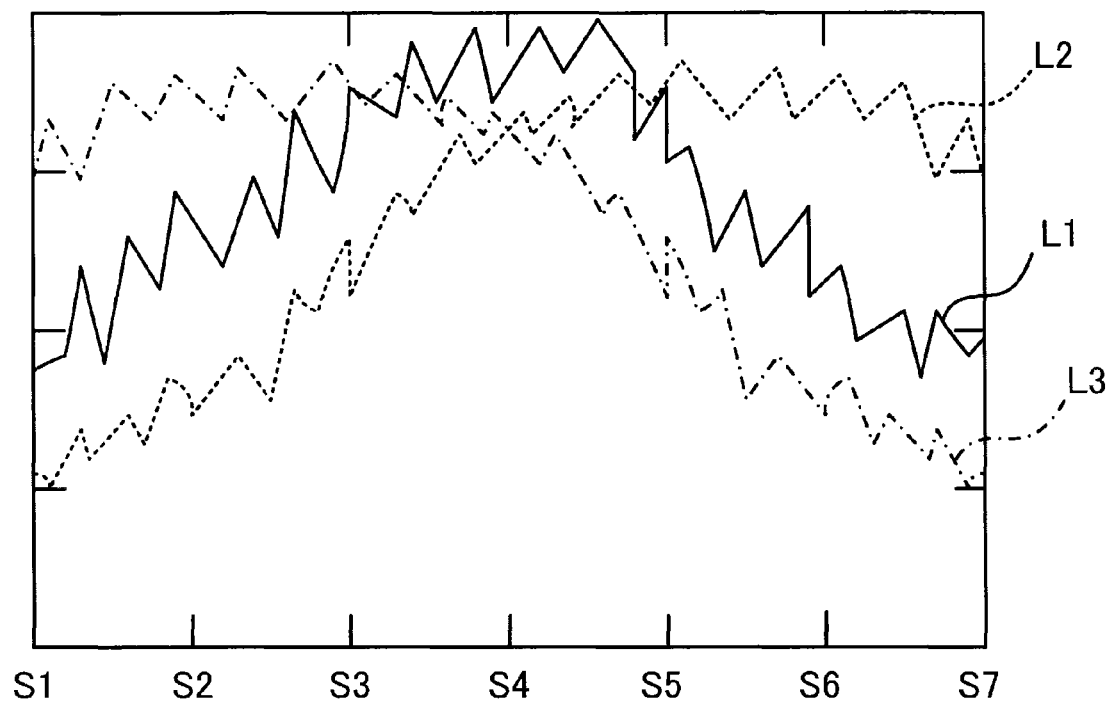
FIG. 5A is a schematic view showing an outline of the ultrasound diagnosis apparatus as an embodiment.
Figure 5B:
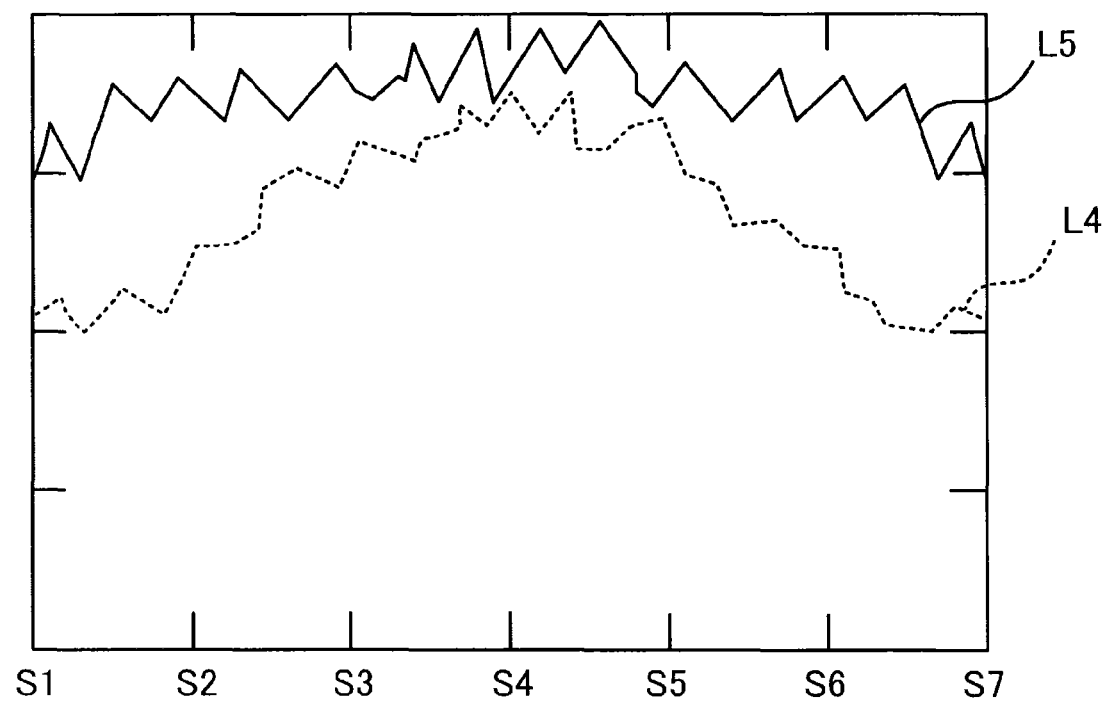
FIG. 5B is a schematic view showing an outline of the ultrasound diagnosis apparatus as an embodiment.

In addition, FIG. 5A is a graph showing the magnitudes of pixel values respectively in image P1, image P2 and image P3 with respect to the arc from position S1 to position S7 along the contour C. For clarity in illustration, FIG. 3 shows the contour C a little away from the part R. The horizontal axis indicates the position from position S1 to position S7, and the vertical axis indicates the magnitudes of pixel values. Line L1 represents the distribution of pixel values in image P1; line L2 represents the distribution of pixel values in image P2; and line L3 represents the distribution of pixel values in image P3. FIG. 5B is a graph showing the distributions of pixel values, respectively, after the arithmetic mean and after the highest selection with respect to the arc from position S1 to position S7 along the contour C. Line L4 indicates the values obtained by the arithmetic mean on pixel values in image P1, image P2 and the image P3. Line L5 indicates the values obtained by the highest selection on pixel values in image P1, image P2 and the image P3.

Contour is a part where acoustic impedance changes greatly. If the contour is emphasized in the composition image data, viewability is improved of the image based on the composition image data. Respective undulations of line L1, line L2 and line L3 schematically show pixel value distributions in the transmission and reception directions and unevenness of pixel values caused by speckle noise. In image P1, which has been generated based on transmission and reception direction D1, pixel values are high in the vicinity of position S4, where the contour C is perpendicular to transmission and reception direction D1, and pixel values decrease as the position along the contour goes away from position S4. In addition, in image P2, which has been generated based on transmission and reception direction D2, pixel values are high in the vicinity of position S5, where the contour C is perpendicular to transmission and reception direction D2, and pixel values decrease as the position along the contour goes away from position S5. In addition, in image P3, which has been generated based on transmission and reception direction D3, pixel values are high in the vicinity of position S3, where the contour C is perpendicular to transmission and reception direction D3, and pixel values decrease as the position along the contour goes away from position S3.

FIG. 5B is a graph showing the distributions of pixel values processed, respectively, by the arithmetic mean and by the highest selection with respect to the arc from position S1 to position S7 along the contour C. The horizontal axis indicates the position from position S1 to position S7, and the vertical axis indicates the magnitudes of pixel values. In the pixel value distribution by the arithmetic mean shown by line L4, the unevenness caused by speckle noise of the pixel values is reduced from those indicated by line L1, line L2 and line L3. The distribution of the pixel values, however, shows a tendency similar to that shown by line L1 but does not show any values to enhance the contour C around the positions where line L2 and line L3 show large pixel values.

On the other hand, in the pixel value distribution by the highest selection shown by line L5, pixel values are high in all positions. Assigning pixel values obtained by the highest selection as pixel values for the contour C in the composition image data means the emphasizing of the pixel values representing is the contour C. As a result, the contour C in the composition image data is enhanced, improving the viewability of the image on the composition image data.

Figure 6A:
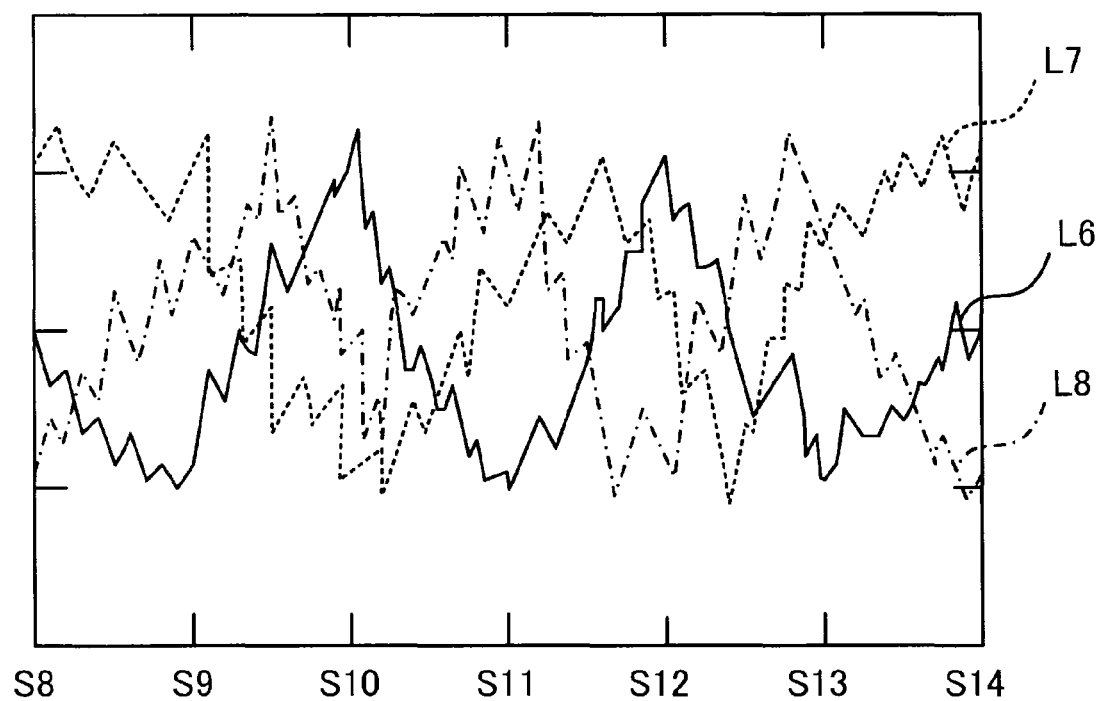
FIG. 6A is a schematic view showing an outline of the ultrasound diagnosis apparatus as an embodiment.
Figure 6B:
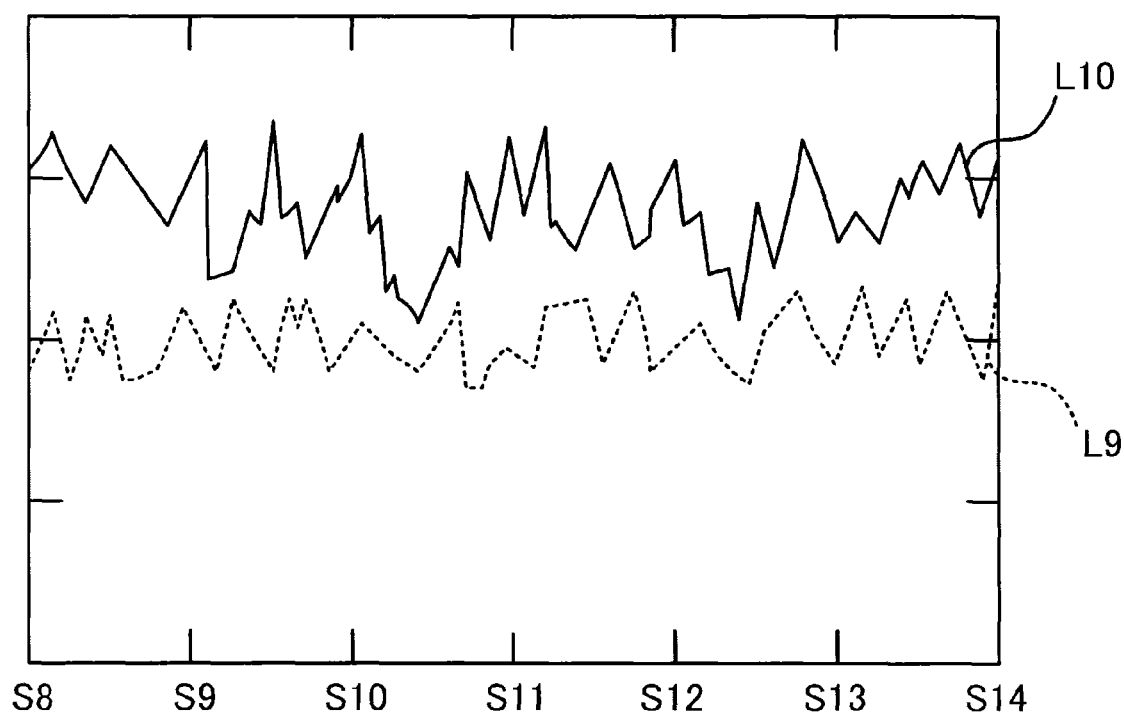
FIG. 6B is a schematic view showing an outline of the ultrasound diagnosis apparatus as an embodiment.

In addition, FIG. 6A is a graph showing the magnitudes of pixel values respectively in image P1, image P2 and image P3 with respect to the line from position S8 to position S14 inside the part R. The horizontal axis indicates the position from position S8 to position S14, and the vertical axis indicates the magnitudes of pixel values. Line L6 represents the distribution of pixel values in image P1; line L7 represents the distribution of pixel values in image P2; and line L8 represents the distribution of pixel values in image P3. FIG. 6B is a graph showing the distributions of pixel values processed, respectively, by the arithmetic mean and by the highest selection with respect to the line from position S8 to position S14 inside the part R. The horizontal axis indicates the position from position S8 to position S14, and the vertical axis indicates the magnitudes of pixel values. Line L9 indicates the values obtained by the arithmetic mean on pixel values in image P1, image P2 and image P3 while line L10 indicates the values obtained by the highest selection on pixel values in image P1, image P2 and image P3.

The inside of the part R is not the place where acoustic impedance changes greatly. If the unevenness of pixel values in position S8 through position S14 is reduced in composition image data, then the viewability of the image on the composition image data will improve. From position S8 to position S14, line L6, line L7, and line L8 show undulations indicating the unevenness of pixel values caused by speckle noise but do not show any pixel value change that is influenced by the transmission and reception direction.

In the pixel value distribution by the arithmetic mean shown by line L9, the unevenness of pixel values caused by speckle noise is reduced from those shown by line L6, line L7 and line L8. For the composition image data, applying the pixel values obtained by the arithmetic mean to the pixels representing the part from position S8 to position S14 is equivalent to reducing the unevenness of pixel values over these positions. As a result, the unevenness of pixel values is reduced over different positions in the part R, and the viewability is improved of the image on the composition image data.

Incidentally, the example explained here involves the generation of image data based on three transmission and reception directions for a part having a circular cross-section, and the application of the highest selection to the pixels representing a common contour and of the arithmetic mean to the pixels representing no common contour as methods of image-synthesis. However, other methods of image-synthesis may be applied. For example, such other methods include the weighting addition, median selection, and lowest selection. The synthesizer 224 accepts the setup of methods of image-synthesis to be applied respectively to the pixels representing a common contour and to the pixels representing no common contour, and the synthesizer 224 generates composition image data based on the set methods of image-synthesis.

In addition, these methods of image-synthesis may be preset in the synthesizer 224 for each part of the subject to be scanned. For example, if the part is the liver, then the highest selection may be applied for the common contour, and the arithmetic mean may be applied for part other than the common contour. Also, if the part is the muscle, then the highest selection may be applied for the common contour, and the lowest selection may be applied for part other than the common contour.

Furthermore, the methods of image-synthesis applied for the common contour and for part other than the common contour may be a method for generating a composition image by weighting a plurality of composition images. For example, the part other than the common contour may be rendered with a method of image-synthesis that applies the weighting addition to the arithmetic mean and median selection, to generate a new composition image.

(Third Storage 225)

The third storage 225 stores image data by the scan-converter 221. The third storage 225 stores tissue-structure information by the first structural information acquirer 222. The third storage 225 stores common structural information by the second structural information acquirer 223. The third storage 225 stores intermediate composition image data by the intermediate composer 226. The third storage 225 stores a composition map by the composition mapper 227.

(Second Storage 23)

The second storage 23 receives composition image data from the composition data unit 228 and stores it.

(Display Controller 24)

The display controller 24 reads composition image data out of the second storage 23 and causes the display 3 to display an image based on the composition image data, which have been read out.

(System Controller 25)

The system controller 25 controls the actions of all parts of the ultrasound diagnosis apparatus. The system controller 25 stores, in advance, computer programs for execution of the functions of all parts of the ultrasound diagnosis apparatus. The system controller 25 executes the computer programs for realization of the functions. For example, the system controller 25 accepts through the operation unit 4 a setup of transmission and reception conditions by the user, and outputs the set transmission and reception conditions to the transmission and reception controller 211.

(Display 3)

The display 3 displays an image based on the composition image data that the display controller 24 has read out. For example, the display 3 comprises a display device like CRT (Cathode Ray Tube) or LCD (Liquid Crystal Display).

(Operation Unit 4)

The operation unit 4 accepts operations by the user and, through the system controller 25, inputs signals and information that correspond to the contents of the operation, to corresponding parts of the apparatus. For example, the operation unit 4 is configured with a keyboard, a mouse, a touch panel. etc.

[Actions]

Figure 7:
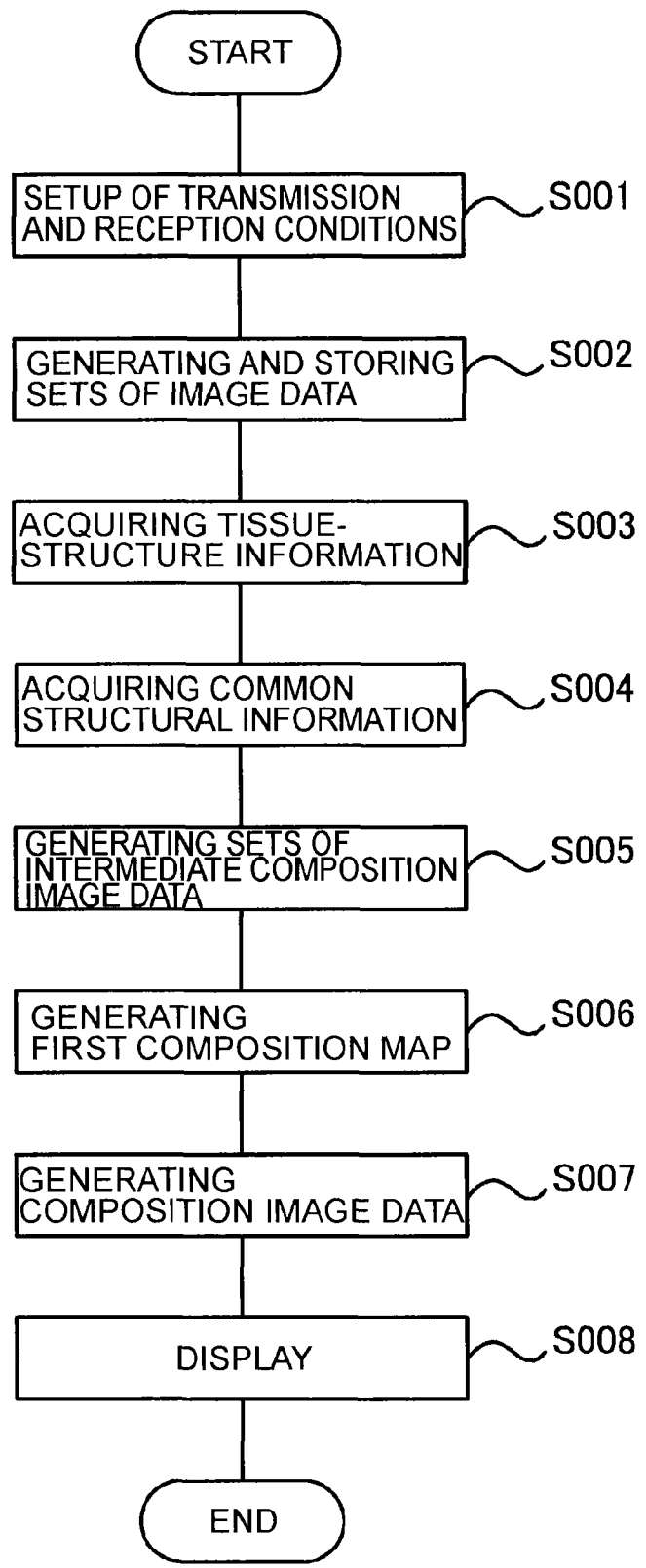
FIG. 7 is a flowchart showing actions taken by the ultrasound diagnosis apparatus as an embodiment.

FIG. 7 is a flowchart showing actions taken by the ultrasound diagnosis apparatus as the embodiment.

(Step S001)

The system controller 25 accepts a setup of transmission and reception conditions by the user through the operation unit 4 and outputs the set transmission and reception conditions to the transmission and reception controller 211. The transmission and reception controller 211 receives the transmission and reception conditions from the system controller 25 and stores them.

(Step S002)

The image generator 216 generates sets of image data whose images represent at least partially a common area for the respective transmission and reception conditions, based on ultrasound waves transmitted and received in accordance with the transmission and reception conditions. In addition, for each of the transmission and reception conditions, the scanner 21 stores, a corresponding set of image data in the first storage 217.

(Step S003)

The scan-converter 221 reads the image data out of the first storage 217. The scan-converter 221 converts the image data, which are represented in columns of signals by scanning line, into those to be displayed in a coordinate system. The scan-converter 221 outputs the converted image data to the third storage 225, which stores them. In addition, the first structural information acquirer 222 reads the image data out of the third storage 225 and acquires tissue-structure information present in the image data. The first structural information acquirer 222 outputs the acquired tissue-structure information to the third storage 225, which stores it. Incidentally, step S003 corresponds to an example of the "step of acquiring first structural information" in the embodiment of a method of processing medical images.

(Step S004)

The second structural information acquirer 223 acquires common structural information, which is common in the sets of image data, based on the tissue-structure information. The second structural information acquirer 223 outputs the acquired common structural information to the third storage 225, which stores it. Incidentally, step S004 corresponds to an example of the "step of acquiring second structural information" in the embodiment of a method of processing medical images.

(Step S005)

The intermediate composer 226 reads a plurality of sets of image data out of the third storage 225 and generates sets of intermediate composition image data, each set being a composition of the sets of image data generated by a corresponding one of the methods of image-synthesis applied. The intermediate composer 226 outputs the generated intermediate composition image data to the third storage 225, which stores them.

(Step S006)

The composition mapper 227 reads the common structural information and the intermediate composition image data out of the third storage 225. The composition mapper 227 then generates a first composition map that indicates the intermediate composition image data in relation to their respective coordinates. The composition mapper 227 outputs the generated first composition map to the third storage 225, which stores it.

(Step S007)

The composition data unit 228 reads the first composition map and the intermediate composition image data out of the third storage 225. The composition data unit 228 then generates composition image data based on the first composition map. The composition data unit 228 outputs the generated composition image data to the second storage 23.

Incidentally, step S005, step S006, and step S007 correspond to examples of the "step of generating" in the embodiment of a method of processing medical images.

(Step S008)

The display controller 24 reads the composition image data out of the second storage 23 and causes the display 3 to display an image based on the composition image data, which have been read out.

[Effects]

Now, description is about the effects of the ultrasound diagnosis apparatus as this embodiment. The ultrasound diagnosis apparatus as this embodiment comprises an image generator 216, a first structural information acquirer 222, a second structural information acquirer 223, and a synthesizer 224. The image generator 216 generates, based on ultrasound waves transmitted and received in accordance with a plurality of transmission and reception conditions, sets of image data whose images represent at least partially a common area for the respective transmission and reception conditions. The first structural information acquirer 222 acquires tissue-structure information indicative of tissue structures depicted, respectively, in the sets of image data. The second structural information acquirer 223 acquires, based on the tissue-structure information, common structural information indicative of a tissue structure common in the sets of image data. The synthesizer 224 applies different methods of image-synthesis on the sets of image data, respectively, one method for a corresponding one of the image areas distinguished based on the common structural information so as to generate composition image data based on the sets of image data. In this way, the ultrasound diagnosis apparatus finds a common structure present in a plurality of sets of image data, each set of image data having been acquired on a corresponding one of the transmission and reception conditions, and applies different methods of image-synthesis, one method to the pixels representing the common structure and another to the pixels representing no common structure, in order to generate a composition image. As a result, the ultrasound diagnosis apparatus can provide an improved viewability to the tissue structure depicted in the image.

Variant Embodiment of the First Embodiment

This variant embodiment is different from the first embodiment in the processing steps performed by the second structural information acquirer 223 and by the synthesizer 224. The following description, therefore, concerns particularly on the matters different from those of the first embodiment.

The second structural information acquirer 223 acquires common structural information in divisions of a plurality of ranks, based on the tissue-structure information. In this case, the second structural information acquirer 223 reads a plurality of sets of tissue-structure information out of the third storage 225. The second structural information acquirer 223 multiplies the pixel values of pixels that are at the same respective coordinates in the sets of tissue-structure information read out. The second structural information acquirer 223 executes this multiplication on each pixel. In the common structural information, the pixel values of pixels representing a common structure are enhanced. In addition, the second structural information acquirer 223 divides the pixel values into a plurality of sections and classifies the pixels representing a common structure by the sections, into a plurality of ranks. Such sections are preset in the second structural information acquirer 223. The ranks of this classification indicate contour tendency with respect to the respective pixels representing the common structure. For example, the larger the pixel value in the common structural information, the higher it is set in the ranks. In this case, the higher in the ranks, the closer the pixel is located to the contour of the common structure in the coordinate system.

As for the pixels representing the common structure indicated by the common structural information, the synthesizer 224 generates composite data by applying different methods of image-synthesis in accordance with the respective ranks of the pixels indicated in the common structural information. The methods of image-synthesis here include two or more of the following: arithmetic mean in which the means of pixel values in the sets of image data are set as pixel values for the composition image data; highest selection in which the maximum values of pixel values in the sets of image data are set as pixel values for the composition image data; weighting addition in which the values obtained by weighting and adding pixel values in the sets of image data are set as pixel values for the composition image data; median selection in which the median values in the sets of image data are set as pixel values for the composition image data; and lowest selection in which the minimum values of pixel values in the sets of image data are set as pixel values for the composition image data. The synthesizer 224 generates a plurality of sets of intermediate composition image data, each set being a composition of the sets of image data by a corresponding one of the methods of image-synthesis applied, and generates a second composition map, which relates the ranks indicated in the common structural information to weighting factors for the sets of intermediate composite data, and then generates composition image data based on the second composition map.

In the composition mapper 227, the weighting factors are preset for the methods of image-synthesis, each of which methods is applied to a corresponding one of the ranks of the pixels representing a common structure, with the ranks being indicated in the common structural information. In addition, in the composition mapper 227, also preset is the method of image-synthesis that is applied to the pixels representing no common structure. The composition mapper 227 relates the weighting factors for the methods of image-synthesis, each method applied to a corresponding one of the ranks of the pixels representing a common structure, to the coordinates of the respective pixels. As a result, the intermediate composition image data generated by the methods of image-synthesis with the weighting factors are related to the coordinates of the pixels representing a common structure. In addition, the composition mapper 227 relates the intermediate composition image data generated by the method of image-synthesis applied to the pixels representing no common structure to the coordinates of the pixels representing no common structure. In this way, the composition mapper 227 generates the second composition map, which indicates the intermediate composition image data generated by the methods of image-synthesis with the weighting factors related to the coordinates of the pixels representing a common structure and which indicates the intermediate composition image data related to the coordinates of the pixels representing no common structure. The composition mapper 227 outputs the generated second composition map to the third storage 225, which stores it.

The composition data unit 228 generates composition image data based on the second composition map. The composition data unit 228 reads the second composition map and the intermediate composition image data out of the third storage 225. Of the coordinates on the second composition map, the composition data unit 228 treats the coordinates related to the weighting factors as the coordinates of the common structure and the coordinates not related to any weighting factor as the coordinates of the part other than the common structure. As for the coordinates of the common structure, the composition data unit 228 executes a process in which the weighting addition is performed on the pixel values of the pixels at the respective coordinates in the sets of intermediate composition image data, which are linked respectively with the weighting factors related to the coordinates. Then, the values obtained by the weighting addition based on the weighting factors are set as the pixel values for the pixels at the corresponding coordinates in the composition image data. In addition, of the coordinates on the second composition map, the composition data unit 228 executes a process that sets the pixel values of the pixels at the coordinates in the intermediate composition image data which coordinates are for the part other than the common structure, as the pixel values for the pixels at the corresponding coordinates in the composition image data. The composition data unit 228 generates composition image data by executing these processes for all coordinates.

For example, the weighting factors are set for the arithmetic mean and the highest selection as methods of image-synthesis and are set such that the higher the common structure in the ranks, the heavier the weight is set for the highest selection, and the lower in the ranks, the heavier the weight is set for the arithmetic mean. On the second composition map, the intermediate composition image data generated by the arithmetic mean are related to the coordinates of the part other than the common structure. In this case, the contribution of the pixel values by the highest selection increases as it goes from the coordinates far-off from the contour to the coordinates close to the contour of the common structure. As a result, pixel values are enhanced more strongly at the coordinates closer to the contour. In addition, since the pixel values by the arithmetic mean are employed for the coordinates of the part other than the common structure, there is less speckle noise there than for the common structure.

In this way, the ultrasound diagnosis apparatus of this variant embodiment classifies the pixels representing a common structure into the ranks and sets the values obtained by the addition of the pixel values in the sets of intermediate composition image data with the weights different for the respective ranks, as the pixel values for the composition image data. As a result, as for the common structure, the pixel values are further emphasized, gradually from the coordinates far-off from the contour to the coordinates close to the contour.

Second Embodiment

[Configuration]

Figure 8:
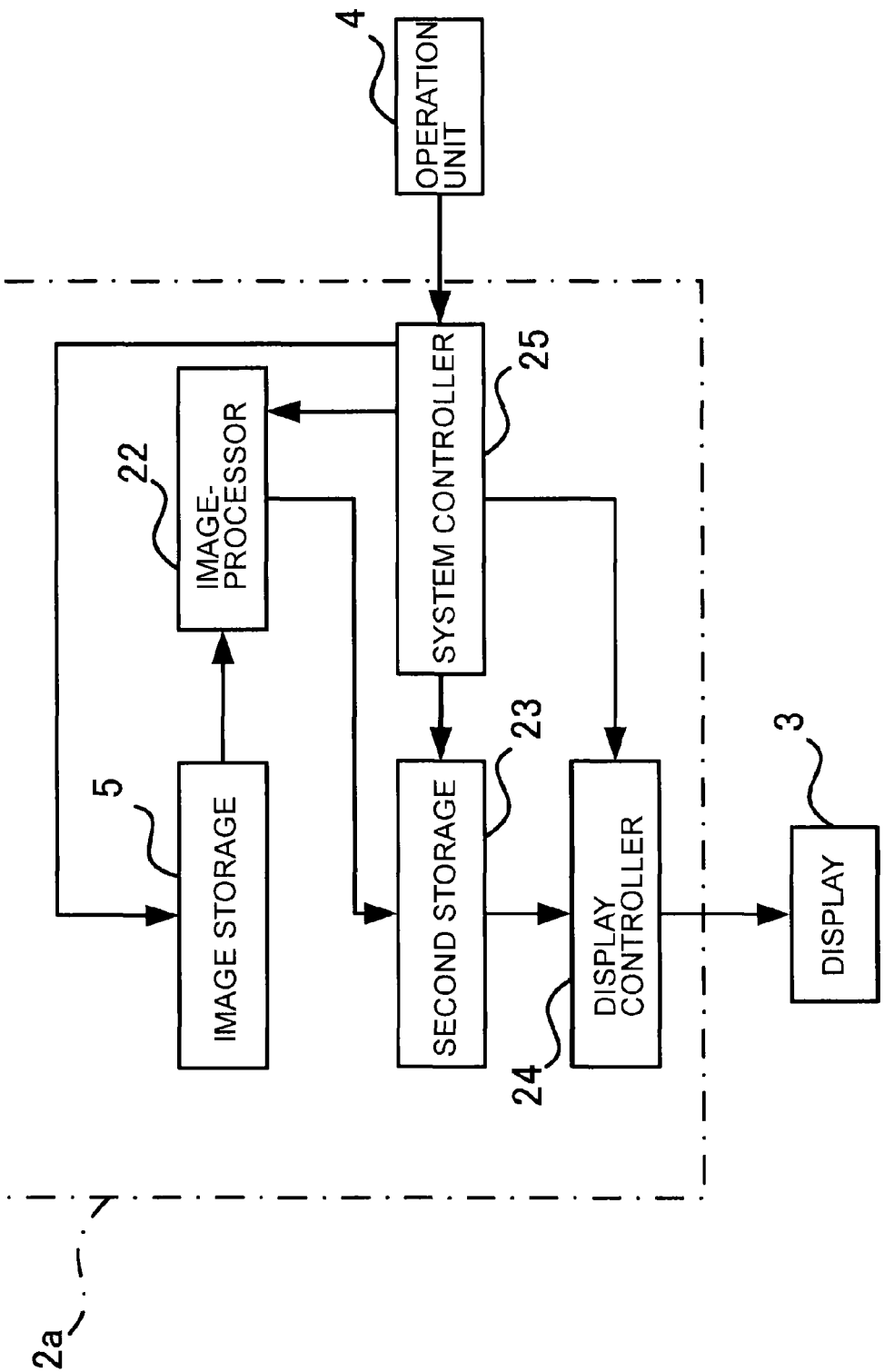
FIG. 8 is a block diagram representing the configuration of a medical image-processing apparatus as an embodiment.

FIG. 8 is a block diagram showing the configuration of a medical image-processing apparatus according to this embodiment. The medical image-processing apparatus comprises a main body 2a, an operation unit 4, and a display 3. The main body 2a comprises an image storage 5, an image-processor 22, a second storage 23, a display controller 24, and a system controller 25. This medical image-processing apparatus has the image storage 5 that replaces the ultrasound probe 1 and the scanner 21, which are in the configuration of the ultrasound diagnosis apparatus of the first embodiment. The following description, therefore, concerns particularly on this matter, which is different from the first embodiment.

The image storage 5 stores in advance a plurality of sets of image data that have been generated, based on ultrasound waves transmitted and received in accordance with a plurality of transmission and reception conditions, each set of image data being for a corresponding one of the transmission and reception conditions, each image for each set of image data at least partially sharing a common area. In other words, the image storage 5 stores, in advance, image data representing tissue structures of the subject that have been acquired for each of the transmission and reception conditions on which the ultrasound waves transmitted and received through the subject are based for the scanning. This means that the image storage 5 stores, in advance, image data that were generated in the past by the transmission-reception compound technique under each of the transmission and reception conditions.

The image-processor 22 comprises a scan-converter 221, a first structural information acquirer 222, a second structural information acquirer 223, a synthesizer 224, and a third storage 225. The scan-converter 221 reads image data out of the image storage 5 and converts the image data read out into data to be displayed in a coordinate system. The scan-converter 221 outputs the converted image data to the third storage 225, which stores them.

The first structural information acquirer 222 reads image data out of the third storage 225, as does the ultrasound diagnosis apparatus of the first embodiment, and acquires tissue-structure information indicative of tissue structures depicted, respectively, in the sets of image data. The second structural information acquirer 223 acquires common structural information indicative of a tissue structure common in the sets of image data, as does the ultrasound diagnosis apparatus of the first embodiment. The synthesizer 224, as does the ultrasound diagnosis apparatus of the first embodiment, then applies different methods of image-synthesis on the sets of image data, each method to a corresponding one of the image areas distinguished based on the common structural information and generates composition image data based on the sets of image data.

[Actions]

FIG. 9 is a flowchart showing actions taken by the medical image-processing apparatus of this embodiment.

(Step S101)

The scan-converter 221 reads image data out of the image storage 5. The scan-converter 221 converts the image data into data to be displayed in a coordinate system. The scan-converter 221 outputs the converted image data to the third storage 225, which stores them. In addition, the first structural information acquirer 222 reads the image data out of the third storage 225 and acquires tissue-structure information indicated in the image data. The first structural information acquirer 222 outputs the acquired tissue-structure information to the third storage 225, which stores it.

(Step S102)

The second structural information acquirer 223 acquires, based on the tissue-structure information, common structural information indicative of a tissue structure common in the sets of image data. The second structural information acquirer 223 outputs the acquired common structural information to the third storage 225, which stores it.

(Step S103)

The intermediate composer 226 reads a plurality of sets of image data out of the third storage 225 and generates sets of intermediate composition image data, each set being a composition of the sets of image data by a corresponding one of the methods of image-synthesis applied. The intermediate composer 226 outputs the generated intermediate composition image data to the third storage 225, which stores them.

(Step S104)

The composition mapper 227 reads the common structural information and the intermediate composition image data out of the third storage 225. The composition mapper 227 generates a first composition map, which indicates the intermediate composition image data in relation to respective coordinates. The composition mapper 227 outputs the generated first composition map to the third storage 225, which stores it.

(Step S105)

The composition data unit 228 reads the first composition map and the intermediate composition image data out of the third storage 225. The composition data unit 228 generates composition image data based on the first composition map. The composition data unit 228 outputs the generated composition image data to the second storage 23.

(Step S106)

The display controller 24 reads the composition image data out of the second storage 23 and causes the display 3 to display an image based on the composition image data read out.

[Effects]

Now, description is about the effects of the medical image-processing apparatus of this embodiment. The medical image-processing apparatus of this embodiment comprises an image storage 5, a first structural information acquirer 222, a second structural information acquirer 223, and a synthesizer 224. The image storage 5 stores, in advance, a plurality of sets of image data that have been generated based on ultrasound waves transmitted and received in accordance with a plurality of transmission and reception conditions, each set of image data having been generated and stored for a corresponding one of the transmission and reception conditions, each image for each set of image data at least partially sharing a common area. The first structural information acquirer 222 acquires tissue-structure information indicative of tissue structures depicted, respectively, in the sets of image data. The second structural information acquirer 223 acquires, based on the tissue-structure information, common structural information indicative of a tissue structure common in the sets of image data. The synthesizer 224 applies different methods of image-synthesis on the sets of image data, respectively, each method to a corresponding one of the image areas distinguished based on the common structural information and, by doing so, generates composition image data based on the sets of image data. In this way, the medical image-processing apparatus calculates a common structure represented commonly in the sets of image data, each set of image data having been acquired on a corresponding one of the transmission and reception conditions, and then generates a composition image by applying different methods of image-synthesis, one method to the pixels representing the common structure and another to the pixels representing no common structure. As a result, it is possible that the medical image-processing apparatus be provided with an improved viewability of tissue structures depicted in images.

It is also possible that a method of processing medical images be so implemented to realize some of the above-mentioned embodiments as a computer program, which can be stored on an arbitrary computer-readable storage medium. Such storage media can include for example, semiconductor memory, optical discs, magneto-optical disks, magnetic storages, etc. In addition, the computer program can be transmitted or received through a network like the Internet or a LAN.

With an ultrasound diagnosis apparatus, a medical image-processing apparatus or a method of processing medical images according to at least one of the above-mentioned embodiments, calculation is made for a common structure represented commonly throughout a plurality of sets of image data, each set of image data having been acquired on a corresponding one of a plurality of transmission and reception conditions. Then, a composition image is generated by applying different methods of image-synthesis, one method to the pixels representing the common structure and another to the pixels representing no common structure. As a result, viewability is improved of the tissue structure depicted in the image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising
an image generator configured to
generate, based on ultrasound waves transmitted and received in accordance with a plurality of transmission and reception conditions, a plurality of two-dimensional images including a common area, the plurality of two-dimensional images being images in a substantially same cross section; and
image-processor configured to
acquire tissue-structure information indicative of a tissue structure from each of the plurality of two-dimensional images;
acquire, based on the tissue-structure information acquired from each of the plurality of two-dimensional images, common structural information indicative of a tissue structure common in the plurality of two-dimensional images;
assign a first method of image-synthesis to a first image area identified by the common structural information for each of the plurality of two-dimensional images, the first method of image-synthesis different from a second method of image-synthesis assigned to a second image area different from the first image area, each of the first and second method of image-synthesis is one of an arithmetic mean in which the mean values of pixel values in the sets of image data are set as pixel values for composition image data, a highest selection in which the maximum values of pixel values in the sets of image data are set as pixel values for the composition image data, a weighting addition in which the values obtained by weighting addition of pixel values in the sets of image data are set as pixel values for the composition image data, a median selection in which the medians of pixel values in the sets of image data are set as pixel values for the composition image data, and a lowest selection in which the minimum values of pixel values in the sets of image data are set as pixel values for the composition image data; and
generate composition image data by composing the plurality of images according to the first and second method of image-synthesis assigned to the first and second image areas, respectively.

2. An ultrasound diagnosis apparatus according to claim 1, wherein
the image-processor is configured to
acquire contour information as the tissue-structure information from each of the plurality of two-dimensional images; and
acquire common contour information that is common in the plurality of two-dimensional images, as the common structural information, based on the contour information.

3. An ultrasound diagnosis apparatus according to claim 2, wherein
the image-processor is configured to
acquire the tissue-structure information by applying a multi-resolution analysis; and
acquire the common structural information based on the tissue-structure information acquired by the multi-resolution analysis.

4. An ultrasound diagnosis apparatus according to claim 3, wherein
the image generator is configured to generate the plurality of two-dimensional images, based on a plurality of transmission and reception directions, a plurality of transmission and reception frequencies, or a plurality of reception-signal processing conditions as the transmission and reception conditions.

5. An ultrasound diagnosis apparatus according to claim 2, wherein
the image generator is configured to generate the plurality of two-dimensional images, based on a plurality of transmission and reception directions, a plurality of transmission and reception frequencies, or a plurality of reception-signal processing conditions as the transmission and reception conditions.

6. An ultrasound diagnosis apparatus according to claim 2, wherein
the image-processor is configured to
generate a plurality of intermediate composition images, which are compositions of the plurality of two-dimensional images, each of the intermediate composition images being generated by a corresponding one of the first and second methods of image-synthesis;
generate a first composition map, which relates any one of the intermediate composition images to the common structural information; and then to generate the composition image based on the first composition map.

7. An ultrasound diagnosis apparatus according to claim 2, wherein
the image-processor is configured to
acquire, based on the tissue-structure information, the common structural information in divisions of a plurality of ranks; and
generate the composition image by applying different methods of the arithmetic mean, the highest selection, the weighting addition, a median selection, and the lowest selection on the pixels represented by the common structure information, each method to a corresponding one of the ranks about the pixels.

8. An ultrasound diagnosis apparatus according to claim 3, wherein
the image-processor is configured to generate a plurality of intermediate composition images, which are compositions of the plurality of two-dimensional images, each of the intermediate composition images being generated by a corresponding one of the first and second methods of image-synthesis;
generate a first composition map, which relates any one of the intermediate composition images to the common structural information; and
then to generate the composition image based on the first composition map.

9. An ultrasound diagnosis apparatus according to claim 3, wherein
the image-processor is configured to
acquire, based on the tissue-structure information, the common structural information in divisions of a plurality of ranks; and
generate the composition image by applying different methods of the arithmetic mean, the highest selection, the weighting addition, a median selection, and the lowest selection on the pixels represented by the common structure information, each method to a corresponding one of the ranks about the pixels.

10. An ultrasound diagnosis apparatus according to claim 1, wherein
the image generator is configured to generate the plurality of two-dimensional images, based on a plurality of transmission and reception directions, a plurality of transmission and reception frequencies, or a plurality of reception-signal processing conditions as the transmission and reception conditions.

11. An ultrasound diagnosis apparatus according to claim 1, wherein
the image-processor is configured to generate a plurality of intermediate composition images, which are compositions of the plurality of two-dimensional images, each of the intermediate composition images being generated by a corresponding one of the methods of image-synthesis; generate a first composition map, which relates any one of the intermediate composition images to the common structural information; and then to generate the composition image data based on the first composition map.

12. An ultrasound diagnosis apparatus according to claim 1, wherein
the image-processor is configured to
acquire, based on the tissue-structure information, the common structural information in divisions of a plurality of ranks; and
generate the composition image by applying different methods of the arithmetic mean, the highest selection, the weighting addition, a median selection, and the lowest selection on the pixels represented by the common structure information, each method to a corresponding one of the ranks about the pixels.

13. An ultrasound diagnosis apparatus according to claim 12, wherein
the image-processor is configured to generate a plurality of intermediate composition images, which are compositions of the plurality of two-dimensional images, each of the intermediate composition images being generated by a corresponding one of the first and second methods of image-synthesis;
generate a second composition map, which relates the ranks of the common structural information to weighting factors for each of the intermediate composition images; and
generate the composition image based on the second composition map.

14. A medical image-processing apparatus comprising processing storage configured to
store in advance a plurality of two-dimensional images that have been generated based on ultrasound waves transmitted and received in accordance with a plurality of transmission and reception conditions, the plurality of two-dimensional images being images in a substantially same cross section, the plurality of two-dimensional images including a common area; and
image-processor configured to
acquire tissue-structure information indicative of a tissue structure from each of the plurality of two-dimensional images;
acquire, based on the tissue-structure information acquired from each of the plurality of two-dimensional images, common structural information indicative of a tissue structure common in the plurality of two-dimensional images;
assign a first method of image-synthesis to a first image area identified by the common structural information for each of the plurality of two-dimensional images, the first method of image-synthesis different from a second method of image-synthesis assigned to a second image area different from the first image area, each of the first and second method of image-synthesis is one of an arithmetic mean in which the mean values of pixel values in the sets of image data are set as pixel values for composition image data, a highest selection in which the maximum values of pixel values in the sets of image data are set as pixel values for the composition image data, a weighting addition in which the values obtained by weighting addition of pixel values in the sets of image data are set as pixel values for the composition image data, a median selection in which the medians of pixel values in the sets of image data are set as pixel values for the composition image data, and a lowest selection in which the minimum values of pixel values in the sets of image data are set as pixel values for the composition image data; and
generate a composition image by composing the plurality of images according to the first and second of image-synthesis assigned to the first and second image areas, respectively.

15. A method of processing medical images, comprising:
acquiring tissue-structure information indicative of a tissue structure from each of a plurality of two-dimensional images that have been generated based on ultrasound waves transmitted and received in accordance with a plurality of transmission and reception conditions, the plurality of two-dimensional images being images in a substantially same cross section, the plurality of two-dimensional images including a common area;

acquiring common structural information is acquired indicative of a tissue structure common in the plurality of two-dimensional images, based on the tissue-structure information acquired from each of the plurality of two-dimensional images;

assigning a first method of image-synthesis to a first image area identified by the common structural information for each of the plurality of two-dimensional images, the first method of image-synthesis different from a second method of image-synthesis assigned to a second image area different from the first image area, each of the first and second method of image-synthesis is one of an arithmetic mean in which the mean values of pixel values in the sets of image data are set as pixel values for composition image data, a highest selection in which the maximum values of pixel values in the sets of image data are set as pixel values for the composition image data, a weighting addition in which the values obtained by weighting addition of pixel values in the sets of image data are set as pixel values for the composition image data, a median selection in which the medians of pixel values in the sets of image data are set as pixel values for the composition image data, and a lowest selection in which the minimum values of pixel values in the sets of image data are set as pixel values for the composition image data; and generating composition image data by composing the plurality of images according to the first and second method of image-synthesis assigned to the first and second image areas, respectively.

* * * * *